United States Patent
Zhong et al.

(10) Patent No.: US 10,054,653 B2
(45) Date of Patent: Aug. 21, 2018

(54) MAGNETIC RESONANCE METHOD AND APPARATUS FOR QUANTITATIVE SIMULTANEOUS MULTI-SLICE ASSESSMENT OF TISSUE DISPLACEMENT, DEFORMATION, AND RELATED BIOMARKER PARAMETERS

(71) Applicants: Siemens Healthcare GmbH, Erlangen (DE); Emory University, Atlanta, GA (US)

(72) Inventors: Xiaodong Zhong, Marietta, GA (US); Deqiang Qiu, Brookhaven, GA (US); John Oshinski, Decatur, GA (US); Amit Saindane, Decatur, GA (US)

(73) Assignees: Siemens Healthcare GmbH, Erlangen (DE); Emory University, Atlanta, GA (US)

( * ) Notice: Subject to any disclaimer, the term of this patent is extended or adjusted under 35 U.S.C. 154(b) by 260 days.

(21) Appl. No.: 15/144,882

(22) Filed: May 3, 2016

(65) Prior Publication Data
US 2017/0322275 A1    Nov. 9, 2017

(51) Int. Cl.
*G01R 33/483* (2006.01)
*G01R 33/561* (2006.01)
(Continued)

(52) U.S. Cl.
CPC ........ *G01R 33/4835* (2013.01); *A61B 5/0042* (2013.01); *A61B 5/031* (2013.01);
(Continued)

(58) Field of Classification Search
CPC ............... G01R 33/00; G01R 33/0017; G01R 33/0023; G01R 33/0035; G01R 33/20;
(Continued)

(56) References Cited

U.S. PATENT DOCUMENTS 7,429,861 B2 * 9/2008 Deimling ............... G01R 33/50
    324/307
9,689,948 B2 * 6/2017 Ugurbil .............. G01R 33/5615
(Continued)

OTHER PUBLICATIONS

Korosoglou, Grigorios, et al. "Strain-encoded cardiac MR during high-dose dobutamine stress testing: Comparison to cine imaging and to myocardial tagging." Journal of Magnetic Resonance Imaging 29.5 (2009): 1053-1061.
(Continued)

*Primary Examiner* — Hoai-An D Nguyen

(57) ABSTRACT

Embodiments relate to a magnetic resonance imaging (MRI) technique in which the two-dimensional (2D) Displacement Encoding with Stimulated Echoes (DENSE) imaging technique and the multiband technique are combined to provide a 2D multi-slice quantitative assessment of displacement, deformation, and mechanics indices of tissue. The scan time is equivalent to the short scan time of the conventional single slice 2D imaging while providing spatial volumetric coverage similar to three-dimensional (3D) imaging. The techniques are combined in both the sequence (i.e., data acquisition) and reconstruction sides. Quantification of tissue displacement and motion is achieved through the combination and further evaluation of tissue mechanical properties is provided by calculating different indices based on the displacement and motion values.

18 Claims, 9 Drawing Sheets

(51) Int. Cl.
  *A61B 5/03* (2006.01)
  *A61B 5/055* (2006.01)
  *A61B 5/00* (2006.01)
(52) U.S. Cl.
  CPC .......... *A61B 5/055* (2013.01); *G01R 33/5614* (2013.01); *G01R 33/5616* (2013.01); *A61B 2576/026* (2013.01)
(58) Field of Classification Search
  CPC ................ G01R 33/44; G01R 33/4608; G01R 33/4633; G01R 33/48; G01R 33/483; G01R 33/4833; G01R 33/4835; G01R 33/54; G01R 33/56; G01R 33/5611; G01R 33/5614; G01R 33/5616; G01R 33/565; G01R 33/56554; G01R 33/58; G01R 33/583; G01R 35/00; G01R 35/005; A61B 5/0042; A61B 5/031; A61B 5/055; A61B 2576/026
  USPC ........................................ 324/300, 307, 309
  See application file for complete search history.

(56) References Cited

U.S. PATENT DOCUMENTS

| | | | |
|---|---|---|---|
| 2005/0215881 A1* | 9/2005 | Van Zijl .............. | G01R 33/483 600/410 |
| 2010/0189328 A1* | 7/2010 | Boernert .......... | G01R 33/56375 382/131 |

OTHER PUBLICATIONS

Bansal, Manish, et al. "Feasibility and accuracy of different techniques of two-dimensional speckle based strain and validation with harmonic phase magnetic resonance imaging." Journal of the American Society of Echocardiography 21.12 (2008): 1318-1325.

Setser, Randolph M., et al. "Left ventricular torsional mechanics after left ventricular reconstruction surgery for ischemic cardiomyopathy." The Journal of thoracic and cardiovascular surgery 134.4 (2007): 888-896.

Setser, Randolph M., et al. "Noninvasive assessment of cardiac mechanics and clinical outcome after partial left ventriculectomy." The Annals of thoracic surgery 76.5 (2003): 1576-1585.

Kramer, Christopher M., et al. "Reverse remodeling and improved regional function after repair of left ventricular aneurysm." The Journal of thoracic and cardiovascular surgery 123.4 (2002): 700-706.

Bilchick, Kenneth C., et al. "Cardiac magnetic resonance assessment of dyssynchrony and myocardial scar predicts function class improvement following cardiac resynchronization therapy." JACC: Cardiovascular Imaging 1.5 (2008): 561-568.

Curry, Cecilia W., et al. "Mechanical dyssynchrony in dilated cardiomyopathy with intraventricular conduction delay as depicted by 3D tagged magnetic resonance imaging." Circulation 101.1 (2000): e2-e2.

Amado, Luciano C., et al. "Multimodality noninvasive imaging demonstrates in vivo cardiac regeneration after mesenchymal stem cell therapy." Journal of the American College of Cardiology 48.10 (2006): 2116-2124.

Zhong, Xiaodong, et al. "Tracking brain motion during the cardiac cycle using spiral cine-DENSE MRI." Medical physics 36.8 (2009): 3413-3419.

Zhong, Xiaodong, et al. "Imaging two-dimensional displacements and strains in skeletal muscle during joint motion by cine DENSE MR." Journal of biomechanics 41.3 (2008): 532-540.

Haraldsson, Henrik, et al. "Feasibility of asymmetric stretch assessment in the ascending aortic wall with DENSE cardiovascular magnetic resonance." Journal of Cardiovascular Magnetic Resonance 16.1 (2014): 1.

Aletras, Anthony H., et al. "DENSE: displacement encoding with stimulated echoes in cardiac functional MRI." Journal of Magnetic Resonance 137.1 (1999): 247-252.

Kim, Daniel, et al. "Myocardial Tissue Tracking with Two-dimensional Cine Displacement-encoded MR Imaging: Development and Initial Evaluation 1." Radiology 230.3 (2004): 862-871.

Zhong, Xiaodong, et al. "Imaging three-dimensional myocardial mechanics using navigator-gated volumetric spiral cine DENSE MRI." Magnetic resonance in medicine 64.4 (2010): 1089-1097.

Zhong, Xiaodong, et al. "Comprehensive cardiovascular magnetic resonance of myocardial mechanics in mice using three-dimensional cine DENSE." Journal of Cardiovascular Magnetic Resonance 13.1 (2011): 1.

Spottiswoode, Bruce S., et al. "Tracking myocardial motion from cine DENSE images using spatiotemporal phase unwrapping and temporal fitting." IEEE Transactions on medical imaging 26.1 (2007): 15-30.

Kar, Julia, et al. "Three-dimensional regional strain computation method with displacement encoding with stimulated echoes (DENSE) in non-ischemic, non-valvular dilated cardiomyopathy patients and healthy subjects validated by tagged MRI." Journal of Magnetic Resonance Imaging 41.2 (2015): 386-396.

Setsompop, Kawin, et al. "Blipped-controlled aliasing in parallel imaging for simultaneous multislice echo planar imaging with reduced g-factor penalty." Magnetic Resonance in Medicine 67.5 (2012): 1210-1224.

* cited by examiner

MAGNETIC RESONANCE METHOD AND APPARATUS FOR QUANTITATIVE SIMULTANEOUS MULTI-SLICE ASSESSMENT OF TISSUE DISPLACEMENT, DEFORMATION, AND RELATED BIOMARKER PARAMETERS

TECHNOLOGY FIELD

The present invention relates generally to acquisition of magnetic resonance images, and more particularly to a simultaneous multi-slice approach for data acquisition and image reconstruction

BACKGROUND

Many diseases influence displacement, deformation, and mechanics indices, such as strain, twist, and torsion, of the tissue or organ compared to the normal status. Quantitative assessment of these biomarker parameters indices is of growing interest and importance. For example, quantitative imaging of myocardial motion and strain in the cardiovascular system is an emerging field as it helps to understand and measure the complex moving and contraction patterns of the heart and vessels can be helpful in both research and clinical settings.

In addition to conventional applications, such as ischemia detection and evaluation of myocardial mechanics related to cardiac surgery, newer applications include quantifying mechanical dyssynchrony in heart failure and measuring the functional effects of experimental therapies such as stem cell infusion. Other clinical applications include evaluation of brain motion, characterization of skeletal muscle contraction, and assessment of vessel wall deformation and stretching. Therefore, the rapid and accurate evaluation of displacement and subsequent deformation and mechanics indices in tissue is of great clinical interest.

Magnetic resonance imaging (MRI) has been used for this purpose. Displacement Encoding with Stimulated Echoes (DENSE) is an MRI technique for quantitative imaging of tissue motion. This technique encodes tissue displacement into the phase of the magnetic resonance (MR) signal. Displacement or motion values can be extracted from the MR phase images for each displacement encoded direction, and combined to generate a displacement map. The displacement values can be further used to calculate the deformation and mechanics indices including but not limited to strain, twist, and torsion.

The DENSE technique that is three-dimensional (3D) both with respect to spatial coverage and motion measurement is beneficial for a complete assessment of tissue motion, especially for organs with complex movement or deformation patterns, such as the heart. However, 3D acquisition usually requires a prolonged scan time that is not preferable and/or not feasible in the clinical environment. Due to this scan time consideration, quantitative two-dimensional (2D) DENSE imaging is more common than 3D DENSE imaging. However, there is a trade-off in using 2D DENSE imaging—lack of volumetric spatial coverage of the organ. Alternatively, 2D DENSE imaging can be performed in multiple slice locations, one slice at a time, to provide the desired spatial coverage, but again at the cost of scan time.

A simultaneous multi-slice 2D imaging technique is capable of acquiring data from multiple slices with no or minimal penalty of scan time compared to a single slice 2D imaging method. In conventional 2D imaging in MRI, multiple slices are acquired sequentially or in an interleaved manner. In the simultaneous, multiband approach, multiple slices are acquired simultaneously and thereby the acquisition is accelerated. Simultaneous acquisition of multiple slices is achieved through specially-designed RF excitation pulses, as well as related image reconstruction methods.

This document describes a comprehensive approach to provide a 2D multi-slice quantitative assessment of displacement, deformation, and mechanics indices of tissue or organ by combining the DENSE technique and the multiband technique, with the scan time equivalent to the short scan time of the conventional single slice 2D imaging while providing spatial volumetric coverage similar to the 3D imaging.

SUMMARY

Embodiments of the present invention are directed to a magnetic resonance imaging (MRI) approach in which two-dimensional (2D) Displacement Encoding with Stimulated Echoes (DENSE) imaging and a simultaneous multiband imaging technique are combined.

In an embodiment, a magnetic resonance (MR) method of data acquisition and image reconstruction of a tissue comprises: acquiring, by a processor, an in-plane calibration scan for each of a plurality of prescribed slices of the tissue; acquiring, by the processor, a multiband calibration scan with a radio-frequency (RF) excitation pulse, to individually excite each of the plurality of prescribed slices one at a time; performing, by the processor, a Displacement Encoding with Stimulated Echoes (DENSE) sequence of acquisition with a multiband RF excitation pulse simultaneously for each of the plurality of prescribed slices; and generating, at a display processor configured to communicate with the processor, images of each of the plurality of prescribed slices based on the DENSE sequence of acquisition.

In an embodiment, acquiring the multiband calibration scan comprises obtaining coil sensitivity information for a receiver coil comprised of a plurality of coil elements for performing the DENSE sequence of acquisition. In an embodiment, the coil sensitivity information comprises calibration coefficients for the image reconstruction. According to an embodiment, a different coil sensitivity at different spatial locations is required for each of the plurality of coil elements.

In an embodiment, the method of data acquisition and image reconstruction further comprises deriving, by the processor, one or more measurements and metrics from the generated images, the one or more measurements and metrics related to displacement and movement of the tissue. According to an embodiment, one or more measurements and metrics relate to brain motion to estimate intracranial pressure.

According to an embodiment, the DENSE sequence of acquisition comprises a readout module comprising an imaging sequence adapted to acquire the images, wherein the imaging sequence comprises one of echo planar imaging (EPI), spiral imaging, turbo spin echo imaging, balanced steady state free precession (b-SSFP) imaging, and gradient echo (GRE) imaging.

In an embodiment, the method of data acquisition and image reconstruction further comprises post-processing, at an image data processor, the images of the tissue, wherein post-processing comprises one or more of phase unwrapping, displacement extraction, tissue tracking, temporal fitting, and mechanics indices calculation.

In an embodiment, the images of the tissue are utilized for quantitative assessment of biomarker parameters of tissue and organ, comprising one or more of mechanical properties parameters and time-resolved dynamic parameters.

In yet another embodiment, a magnetic resonance (MR) system for data acquisition and image reconstruction of a tissue comprises: a processor configured to acquire an in-plane calibration scan for each of a plurality of prescribed slices of the tissue; acquire a multiband calibration scan with a radio-frequency (RF) excitation pulse, to individually excite each of the plurality of prescribed slices one at a time; and perform a Displacement Encoding with Stimulated Echoes (DENSE) sequence of acquisition with a multiband RF excitation pulse simultaneously for each of the plurality of prescribed slices. A display processor configured to communicate with the processor generates images of each of the plurality of prescribed slices based on the DENSE sequence of acquisition.

BRIEF DESCRIPTION OF THE DRAWINGS

The foregoing and other aspects of the present invention are best understood from the following detailed description when read in connection with the accompanying drawings. For the purpose of illustrating the invention, shown in the drawings are embodiments that are presently preferred, it being understood, however, that the invention is not limited to the specific instrumentalities disclosed. Included in the drawings are the following Figures.

DETAILED DESCRIPTION

Embodiments relate to a comprehensive approach to provide a two-dimensional (2D) multi-slice quantitative assessment of displacement, deformation, and mechanics indices of tissue or organ by combining the 2D Displacement Encoding with Stimulated Echoes (DENSE) imaging technique and the multiband technique, with the scan time equivalent to the short scan time of the conventional single slice 2D imaging while providing spatial volumetric coverage similar to the 3D imaging. According to embodiments herein, the techniques are combined in both the sequence (i.e., data acquisition) and reconstruction sides. In an embodiment, the displacement, deformations and mechanics parameters of tissues are used for estimating intracranial pressure non-invasively.

As noted above, DENSE is an MRI technique for quantitative imaging of tissue motion. This technique encodes tissue displacement into the phase of the MR signal. Displacement or motion values can be extracted from the MR phase images for each displacement encoded direction, and combined to generate a displacement map. The displacement values can be further used to calculate the deformation and mechanics indices including but not limited to strain, twist, and torsion.

Figure 1:
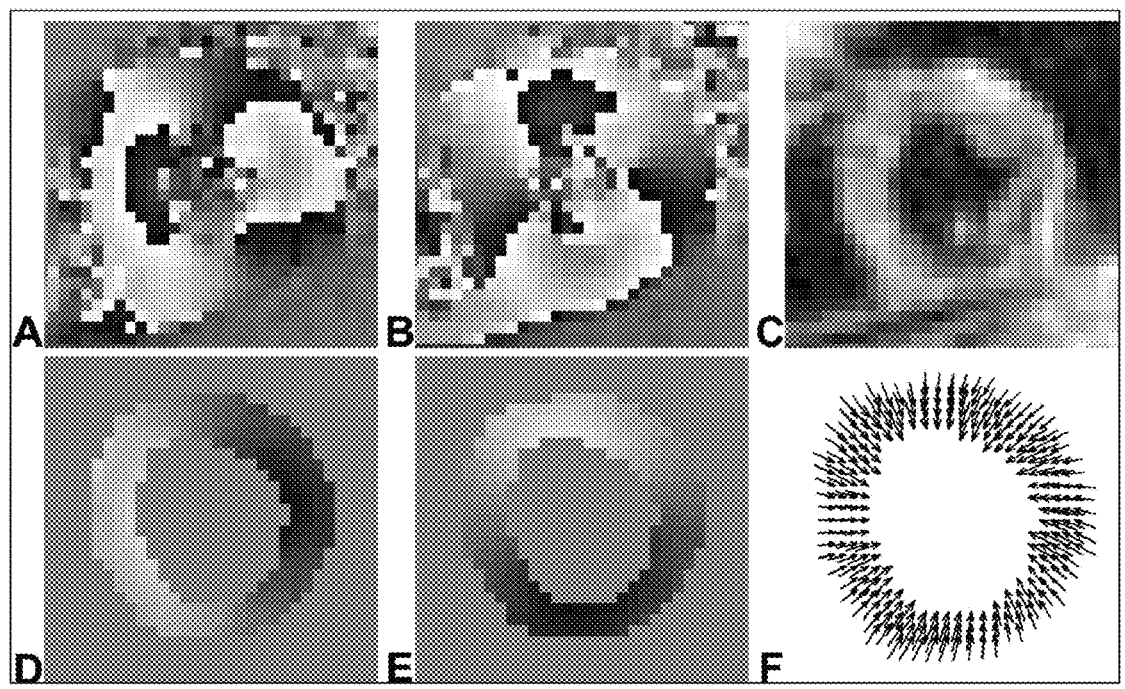
FIG. 1 illustrates example DENSE images and two-dimensional displacement maps of the left ventricle of the heart at end-systole.

With reference to FIG. 1, shown are example DENSE images and the two-dimensional (2D) displacement map of the left ventricle of the heart at end-systole. The left column (A, D) contains the phase images displacement-encoded in the horizontal direction, and the middle column (B, E) contains the phase images displacement-encoded in the vertical direction. The first row contains the phase-reconstructed (A, B) and the magnitude-reconstructed (C) images from the DENSE images acquired directly from the scanner. Phase wrap is seen in the phase-reconstructed images at end-systole (A, B). The second row contains the segmented left ventricle and its unwrapped phase images (D, E) corresponding to (A, B), as well as the resulting 2D displacement map (F).

Figure 2:
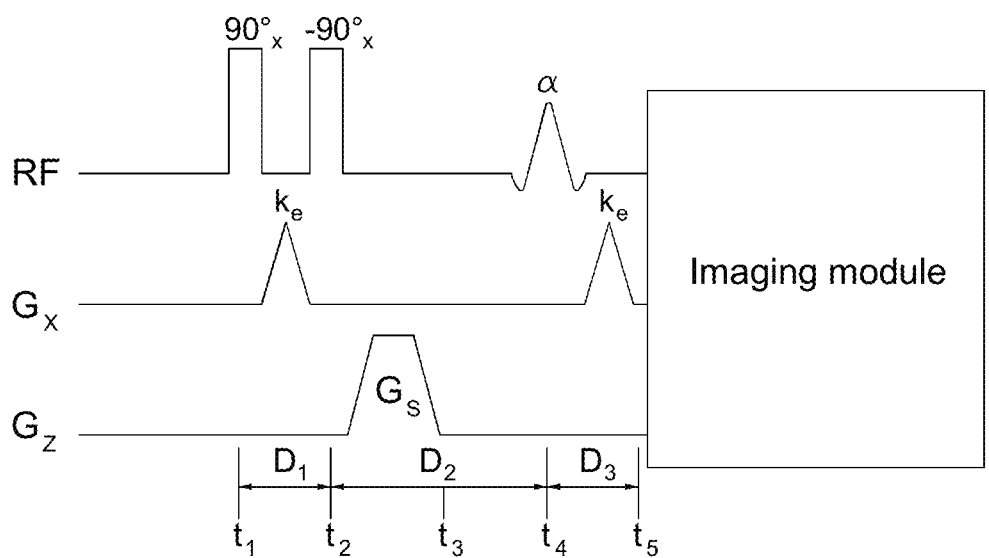
FIG. 2 is a timing diagram of the displacement encoding module in DENSE pulse sequences.

With reference to FIG. 2, an exemplary timing diagram 200 of the displacement encoding module in DENSE pulse sequences, which encodes displacement in the x direction, is shown. RF are the radio-frequency pulses; $G_x$ and $G_z$ are the magnetic gradient field in the x and z direction, respectively. The angle notation $90°_x$ is the rotation about the x-axis by an angle of 90° in the left-hand convention. The RF pulse of $-90°_x$ is accomplished by setting the phase of the RF pulse of $90°_x$ to be 180°. α indicates the rotation about the x-axis by a small flip angle of α. $k_e$ is the spatial frequency imparted by the displacement encoding gradient, which is proportional to the area of the gradient and is given by $$k_e = \frac{\gamma}{2\pi} \int_{t_1}^{t_2} G(\tau) d\tau.$$

$G_s$ is a spoiler gradient. $D_1$-$D_3$ are the time durations, and $t_1$-$t_5$ are the time points.

With continued reference to FIG. 2, the sequence starts with a displacement-encoding module, also referred to as a 1-1 spatial modulation of magnetization (SPAMM) kernel in the tagging sequence, which includes two non-selective 90° RF pulses separated by a displacement-encoding gradient, and followed by a spoiler gradient. This displacement-encoding module can be played out at any time of interest during the cardiac cycle, but is typically done at end-diastole. The displacement-encoding module applies a labelling process on the tissue, which is very similar with the tissue labelling/tagging process in tissue tagging sequences and works with the un-labelling process together to fulfill the purpose of displacement encoding.

The displacement-encoding module is followed by the application of a readout module, which can employ various imaging sequences to sample the k-space after the application of the displacement-decoding gradient, including but not limited to echo planar imaging (EPI) and spiral imaging. This readout module can be adapted to acquire multi-phase or cine data. The flip angle of the slice-selective excitation RF pulse in the readout modules can be either 90° (usually for a single-phase DENSE sequence with only one readout module) or a small flip angle α (usually for the multi-phase or cine DENSE sequence with multiple readout modules), depending on the application. The readout module applies an un-labelling process on the tissue, which works with the previous labelling process in the displacement-encoding module to finish the displacement encoding. An ECG-gated cine DENSE sequence that uses an EPI k-space trajectory is shown in FIG. 3.

Figure 3:
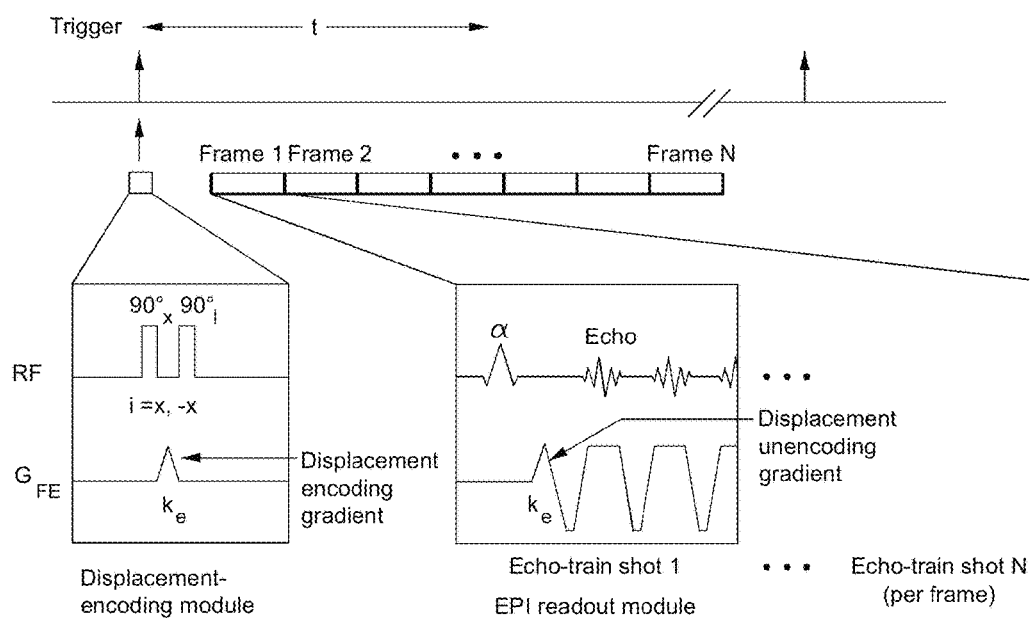
FIG. 3 is a timing diagram of an EPI cine DENSE sequence.

FIG. 3 is a timing diagram 300 of an EPI cine DENSE sequence. In practice, to minimize TE, the displacement unencoding gradients are combined with spatial encoding gradients. The phase of the second 90° RF pulse alters from the x direction to the −x direction, so that a complete dataset for complementary spatial modulation of magnetization (CSPAMM) artifact suppression can be acquired.

The timing diagrams of FIGS. 2 and 3 are exemplary sequences that may be used in accordance with embodiments disclosed herein. Other sequences known to those of skill in the art may alternatively be used.

Figure 4:
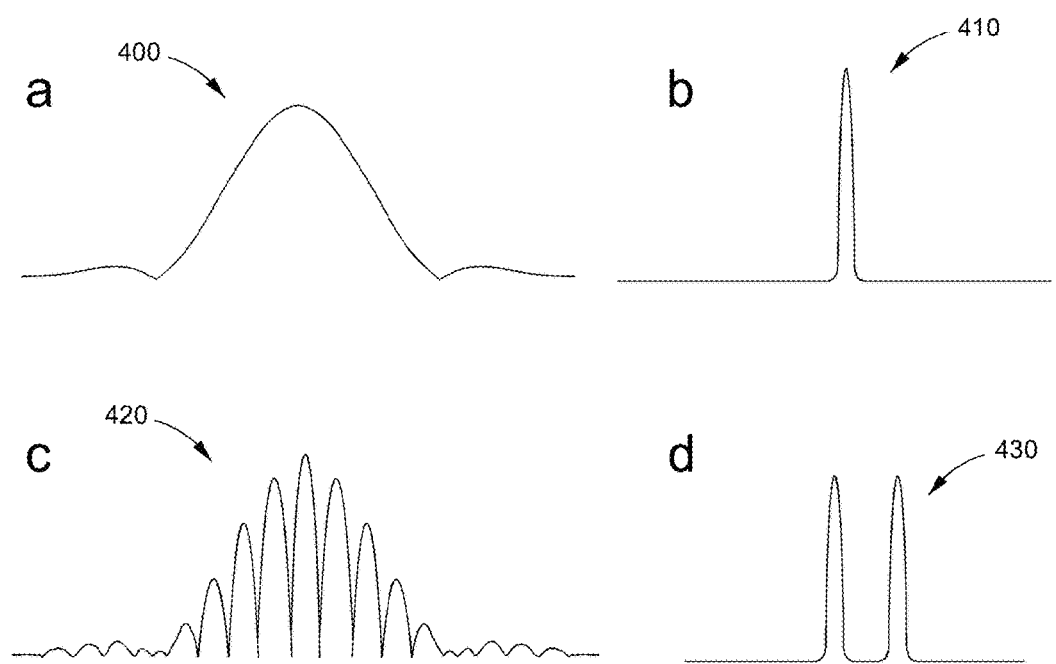
FIG. 4 is a pulse diagram of a simultaneous multiband EPI acquisition module, according to an embodiment.

According to embodiments provided herein, during each phase of the cardiac cycle, a simultaneous multiband EPI acquisition module is added. FIG. 4 illustrates the pulse diagram of the module. A typical shape of a single-band RF excitation pulse 400 is shown in (a), with its corresponding Fourier spectrum density 410 in (b). A multiband RF excitation pulse 420 is shown in (c), with its corresponding Fourier spectrum density 430 in (d). The multiband RF excitation pulse 420 is specially designed so that multiple slices of the anatomical region are simultaneously excited, causing the resultant images to alias onto each other. A receiver coil with multiple coil elements is needed, with different sensitivity to different slice locations. This spatial sensitivity information is acquired through a reference scan before the actual acquisition and used during the image reconstruction phase, as further described below.

Figure 5:
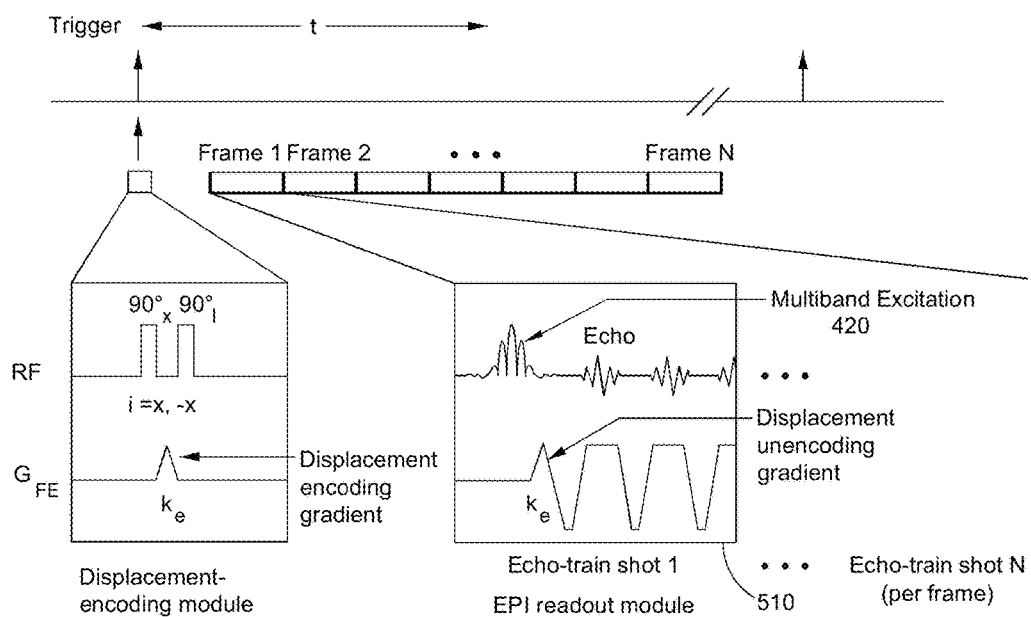
FIG. 5 is a timing diagram of an EPI cine DENSE sequence with a multiband RF pulse, according to an embodiment.

FIG. 5 is a timing diagram 500 of an EPI cine DENSE sequence with the multiband RF excitation pulse 420, according to an embodiment. A simultaneous multiband EPI readout module 510 replaces the conventional single band readout module shown in FIG. 3. Prior to the actual acquisition, a reference scan is acquired to be used in the image reconstruction to resolve individual slices.

According to embodiments provided herein, the combination of the 2D DENSE imaging technique and the multiband technique provides for the acquisition of multi-slice data sufficient for volumetric covering of the tissue within the scan time equivalent to the single slice acquisition with otherwise the same imaging parameters.

According to embodiments provided herein, quantification of tissue displacement and motion is achieved through the combination of the 2D DENSE imaging technique and the multiband technique. Moreover, further evaluation of tissue mechanical properties is provided by calculating different indices based on the displacement and motion values.

Although embodiments disclosed herein are described with reference to a cine DENSE EPI sequence, other sequence types may alternatively be used. It is straightforward to one of ordinary skill in the art to extend and adapt to other sequence types, including, but not limited to, balanced steady state free precession (balanced SSFP or trueFISP) sequence, the spiral sequence, turbo spin echo sequence, and gradient echo (GRE) sequence.

Figure 6:
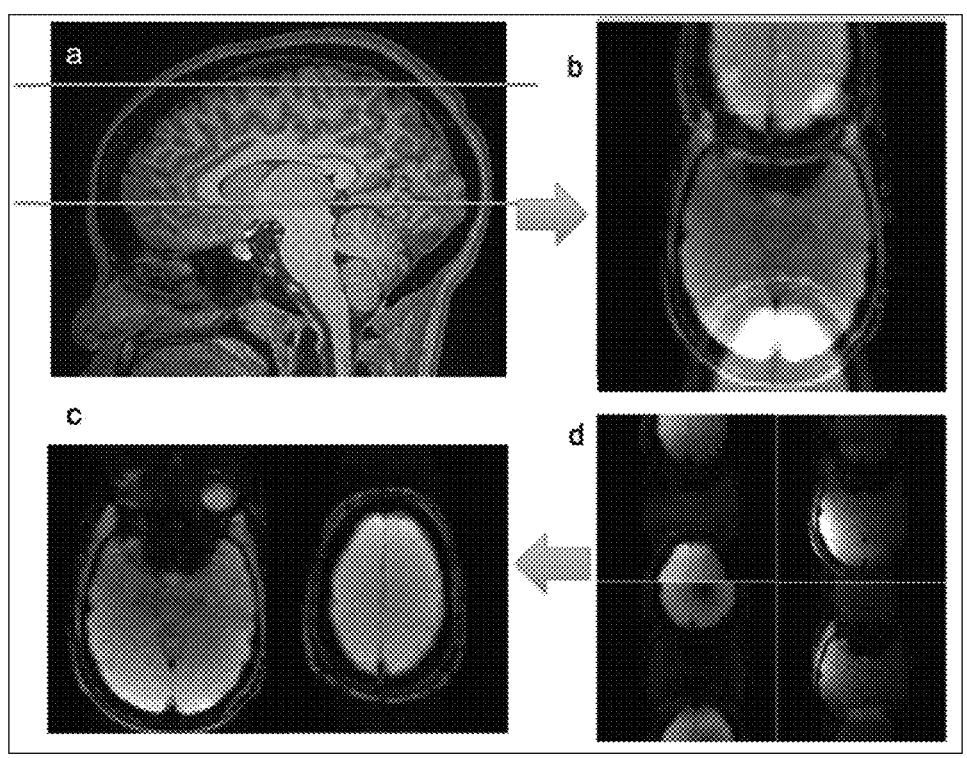
FIG. 6 are diagrams illustrating image reconstruction, according to embodiments.

With reference to FIG. 6, diagrams depicting image reconstruction, according to embodiments provided herein, are provided. Simultaneous excitation of two slices is shown in (a). Using conventional reconstruction methods, the images are aliased with the two slices overlapped, as shown in (b). As can be seen, the two images are merged together.

With continued reference to FIG. 6, using an MRI coil with multiple coil elements (four in the example shown in FIG. 6), each element having a different coil sensitivity at different spatial locations, according to embodiments provided herein, as shown in (d), the two slices are resolved as shown in (c).

Assuming a number of N slices are excited simultaneously and the signal is received with MRI coil with M elements, let $S(x, y, n)$ be the image signal for slice n ($1<n<=N$), and $C(x, y, n, v)$ be the coil sensitivity of element v at location $(x, y)$ for slice n.

During the multiband calibration stage, each slice is excited individually without using a multiband RF pulse. The image signal obtained is expressed as:

$$S_v(x,y,n)=C(x,y,n,v) \cdot S(x,y,n)$$

The "ground-truth" signal intensity $S(x, y, n)$ can be estimated using sum of square of all the signal intensity from all the coil elements:

$$\overline{S(x,y,n)}=\sqrt{\Sigma_v S_v^2(x,y,n)}$$

The coil sensitivity information $C(x, y, n, v)$ can then be estimated.

During the actual image acquisition stage, multiple slices are excited simultaneously and the image signal obtained from coil element v is expressed as:

$$S_v(x,y)=\Sigma_n C(x,y,n,v) \cdot S(x,y,n).$$

This equation is used for each of the M number of coil elements. $S(x, y, n)$ can be estimated by solving this linear equation system using methods such as least square error method, or other known methods.

Figure 7:
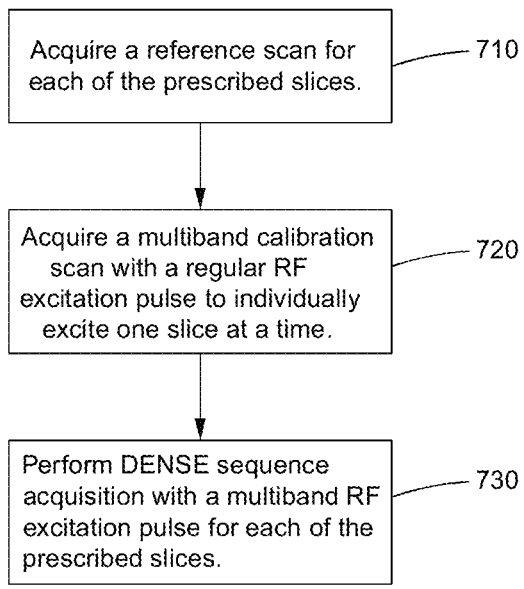
FIG. 7 is a flowchart illustrating a method of data acquisition and image reconstruction, according to embodiments provided herein.

With reference to FIG. 7, a flowchart 700 is provided, illustrating a method of data acquisition and image reconstruction for a tissue, according to embodiments provided herein.

At 710, an in-plane calibration (i.e., reference) scan for each of the prescribed slices of the tissue is acquired. The calibration scan serves to provide a baseline.

At 720, a multiband calibration scan with a regular RF excitation pulse is acquired, to individually excite one slice at a time. Data collected in this step is used to calculate calibration coefficients used for image reconstruction, as described above with reference to FIG. 6.

At 730, DENSE sequence acquisition is performed, with the multiband RF excitation pulse 420 for each of the prescribed slices (i.e., the readout module 510).

With the resultant DENSE image, actual motion of the tissue is encoded. A comparison of this with a reference DENSE image results in a map that measures displacement and movement of the tissue. Various measurements and metrics can be derived, providing a volumetric quantitative assessment of different biomarker parameters or indices of tissue and organ, including mechanical property parameters such as strain, twist, torsion, and time-resolved dynamic parameters such as strain-time curves and time-to-peak.

As one example of an application of the method described herein, metrics related to brain motion may be derived to estimate intracranial pressure. The metrics may include, but are not limited to, torque and propagating speed of motion. The MRI method provided herein for such estimation of intracranial pressure metrics is a significant improvement (time and ease to patient, for example) over the current method requiring lumbar puncture and x-ray guidance.

Additionally, post-processing of the DENSE data may include, but is not limited to, the following sequential steps: phase unwrapping, displacement extraction, tissue tracking, temporal fitting, and mechanics indices calculation such as strain, twist, torsion, and dynamic or time-resolved information. The post-processing, after DENSE data is acquired according to embodiments described herein, may be carried out according to known methods.

Figure 8:
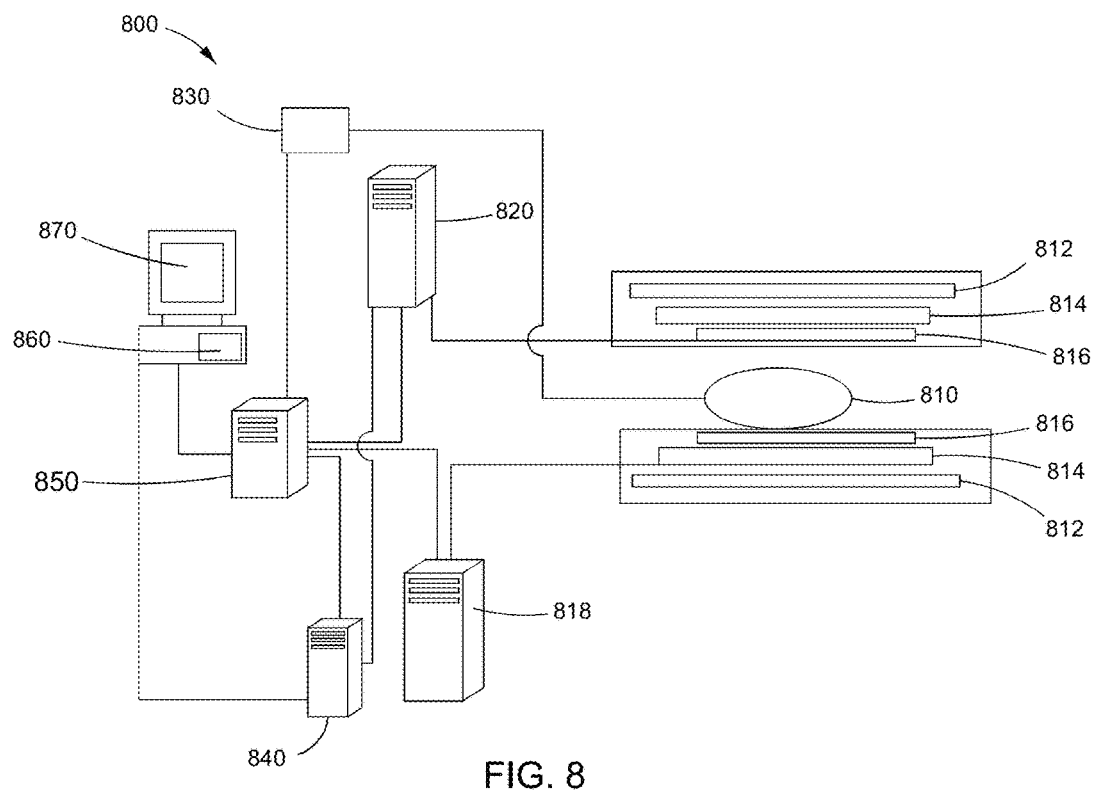
FIG. 8 illustrates a system for data acquisition and image reconstruction, according to embodiments provided herein.

Turning to FIG. 8, a system 800 for data acquisition and image reconstruction, according to embodiments provided herein, is provided. The system 800 includes a source 810 of the tissue, such as a patient. 812, 814, and 816 represent the coils and magnets of an MRI system and are, in an exemplary embodiment, a high field magnet 812, a gradient coil 814, and a radio-frequency (RF) coil 816. Processors 818 (gradient and shim coil controller) and 820 (radio-frequency controller) control the MR magnets and coils. The MRI system components 812, 814, and 816 and processors 818 and 820 depicted in FIG. 8 are one example of an MRI system; other components and processors may be used as known to one of skill in the art to obtain an MR image of tissue.

The system 800 further includes an input processor 830, an image data processor 840, a display processor 860, and an interface 870. A central control system 850 controls the overall operation of and data communication between each of the processors 818, 820, 830, 840, and 860.

Figure 9:
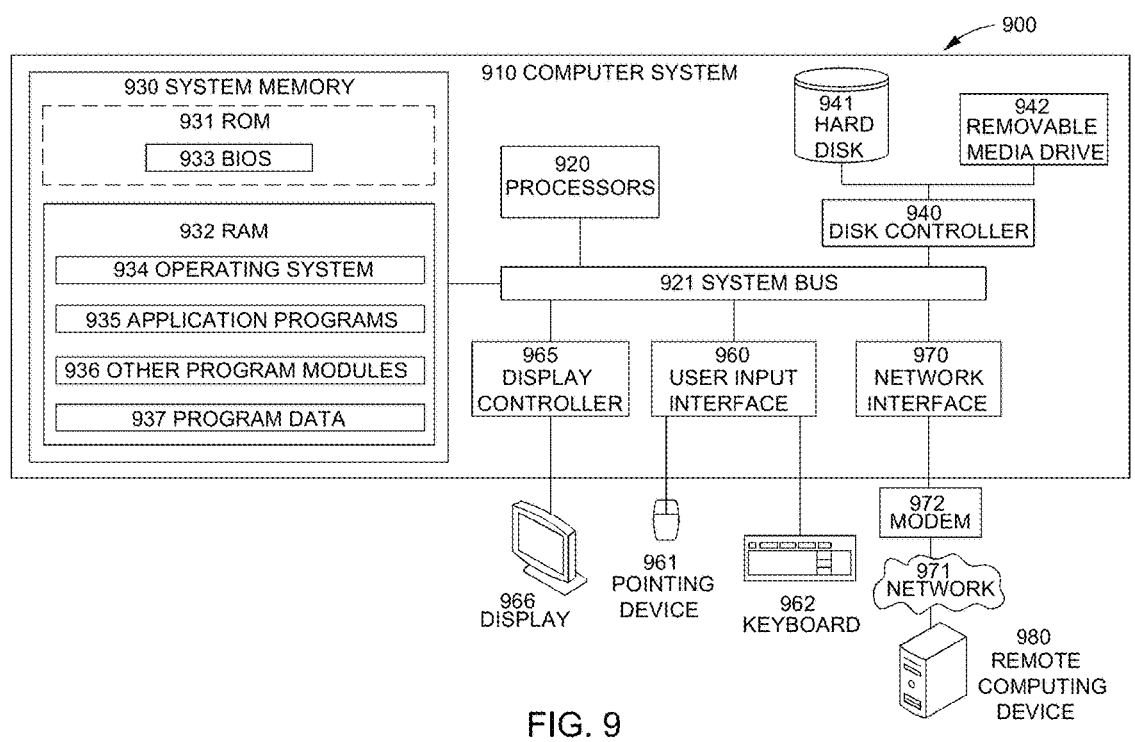
FIG. 9 is an exemplary computing environment in which embodiments disclosed herein may be implemented.

FIG. 9 illustrates an exemplary computing environment 900 within which embodiments of the invention may be implemented. Computing environment 900 may include computer system 910, which is one example of a computing system upon which embodiments of the invention may be implemented. Computers and computing environments, such as computer 910 and computing environment 900, are known to those of skill in the art and thus are described briefly here.

As shown in FIG. 9, the computer system 910 may include a communication mechanism such as a bus 921 or other communication mechanism for communicating information within the computer system 910. The system 910 further includes one or more processors 920 coupled with the bus 921 for processing the information. The processors 920 may include one or more central processing units (CPUs), graphical processing units (GPUs), or any other processor known in the art.

The computer system 910 also includes a system memory 930 coupled to the bus 921 for storing information and instructions to be executed by processors 920. The system memory 930 may include computer readable storage media in the form of volatile and/or nonvolatile memory, such as read only memory (ROM) 931 and/or random access memory (RAM) 932. The system memory RAM 932 may include other dynamic storage device(s) (e.g., dynamic RAM, static RAM, and synchronous DRAM). The system memory ROM 931 may include other static storage device (s) (e.g., programmable ROM, erasable PROM, and electrically erasable PROM). In addition, the system memory 930 may be used for storing temporary variables or other intermediate information during the execution of instructions by the processors 920. A basic input/output system 933 (BIOS) containing the basic routines that help to transfer information between elements within computer system 910, such as during start-up, may be stored in ROM 931. RAM 932 may contain data and/or program modules that are immediately accessible to and/or presently being operated on by the processors 920. System memory 930 may additionally include, for example, operating system 934, application programs 935, other program modules 936 and program data 937.

The computer system 910 also includes a disk controller 940 coupled to the bus 921 to control one or more storage devices for storing information and instructions, such as a magnetic hard disk 941 and a removable media drive 942 (e.g., floppy disk drive, compact disc drive, tape drive, and/or solid state drive). The storage devices may be added to the computer system 910 using an appropriate device interface (e.g., a small computer system interface (SCSI), integrated device electronics (IDE), Universal Serial Bus (USB), or FireWire).

The computer system 910 may also include a display controller 965 coupled to the bus 921 to control a display or monitor 966, such as a cathode ray tube (CRT) or liquid crystal display (LCD), for displaying information to a computer user. The computer system 910 includes an input interface 960 and one or more input devices, such as a keyboard 962 and a pointing device 961, for interacting with a computer user and providing information to the processors 920. The pointing device 961, for example, may be a mouse, a trackball, or a pointing stick for communicating direction information and command selections to the processors 920 and for controlling cursor movement on the display 966. The display 966 may provide a touch screen interface which allows input to supplement or replace the communication of direction information and command selections by the pointing device 961.

The computer system 910 may perform a portion or all of the processing steps of embodiments of the invention in response to the processors 920 executing one or more sequences of one or more instructions contained in a memory, such as the system memory 930. Such instructions may be read into the system memory 930 from another computer readable medium, such as a hard disk 941 or a removable media drive 942. The hard disk 941 may contain one or more datastores and data files used by embodiments of the present invention. Datastore contents and data files may be encrypted to improve security. The processors 920 may also be employed in a multi-processing arrangement to execute the one or more sequences of instructions contained in system memory 930. In alternative embodiments, hardwired circuitry may be used in place of or in combination with software instructions. Thus, embodiments are not limited to any specific combination of hardware circuitry and software.

As stated above, the computer system 910 may include at least one computer readable medium or memory for holding instructions programmed according to embodiments provided herein and for containing data structures, tables, records, or other data described herein. The term "computer readable medium" as used herein refers to any medium that participates in providing instructions to the processors 920 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 941 or removable media drive 942. Non-limiting examples of volatile media include dynamic memory, such as system memory 930. Non-limiting examples of transmission media include coaxial cables, copper wire, and fiber optics, including the wires that make up the bus 921. Transmission media may also take the form of acoustic or light waves, such as those generated during radio wave and infrared data communications.

The computing environment 900 may further include the computer system 910 operating in a networked environment using logical connections to one or more remote computers, such as remote computer 980. Remote computer 980 may be a personal computer (laptop or desktop), a mobile device, a server, a router, a network PC, a peer device or other common network node, and typically includes many or all of the elements described above relative to computer system 910. When used in a networking environment, computer system 910 may include modem 972 for establishing communications over a network 971, such as the Internet. Modem 972 may be connected to system bus 921 via user network interface 970, or via another appropriate mechanism.

Network 971 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 910 and other computers (e.g., remote computing system 980). The network 971 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 971.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A magnetic resonance (MR) method of data acquisition and image reconstruction of a tissue, the method comprising:
   acquiring, by a processor, an in-plane calibration scan for each of a plurality of prescribed slices of the tissue;
   acquiring, by the processor, a multiband calibration scan with a radio-frequency (RF) excitation pulse, to individually excite each of the plurality of prescribed slices one at a time;
   performing, by the processor, a Displacement Encoding with Stimulated Echoes (DENSE) sequence of acquisition with a multiband RF excitation pulse simultaneously for each of the plurality of prescribed slices; and
   generating, at a display processor configured to communicate with the processor, images of each of the plurality of prescribed slices based on the DENSE sequence of acquisition.

2. The method of claim 1, wherein acquiring, by the processor, the multiband calibration scan comprises obtaining coil sensitivity information for a receiver coil comprised of a plurality of coil elements for performing the DENSE sequence of acquisition.

3. The method of claim 2, wherein the coil sensitivity information comprises calibration coefficients for the image reconstruction.

4. The method of claim 2, wherein a different coil sensitivity at different spatial locations is required for each of the plurality of coil elements.

5. The method of claim 1, further comprising deriving, by the processor, one or more measurements and metrics from the generated images, the one or more measurements and metrics related to displacement and movement of the tissue.

6. The method of claim 5, wherein the one or more measurements and metrics relate to brain motion to estimate intracranial pressure.

7. The method of claim 1, wherein the DENSE sequence of acquisition comprises a readout module comprising an imaging sequence adapted to acquire the images, wherein the imaging sequence comprises one of echo planar imaging (EPI), spiral imaging, turbo spin echo imaging, balanced steady state free precession (b-SSFP) imaging, and gradient echo (GRE) imaging.

8. The method of claim 1, further comprising post-processing, at an image data processor, the images of the tissue, wherein post-processing comprises one or more of phase unwrapping, displacement extraction, tissue tracking, temporal fitting, and mechanics indices calculation.

9. The method of claim 1, wherein the images of the tissue are utilized for quantitative assessment of biomarker parameters of tissue and organ, comprising one or more of mechanical properties parameters and time-resolved dynamic parameters.

10. A magnetic resonance (MR) system for data acquisition and image reconstruction of a tissue, the system comprising:
    a processor configured to:
      acquire an in-plane calibration scan for each of a plurality of prescribed slices of the tissue;
      acquire a multiband calibration scan with a radio-frequency (RF) excitation pulse, to individually excite each of the plurality of prescribed slices one at a time; and
      perform a Displacement Encoding with Stimulated Echoes (DENSE) sequence of acquisition with a multiband RF excitation pulse simultaneously for each of the plurality of prescribed slices; and
    a display processor configured to communicate with the processor to generate images of each of the plurality of prescribed slices based on the DENSE sequence of acquisition.

11. The system of claim 10, wherein acquiring, by the processor, the multiband calibration scan comprises obtaining coil sensitivity information for a receiver coil comprised of a plurality of coil elements for performing the DENSE sequence of acquisition.

12. The system of claim 11, wherein the coil sensitivity information comprises calibration coefficients for the image reconstruction.

13. The system of claim 11, wherein a different coil sensitivity at different spatial locations is required for each of the plurality of coil elements.

14. The system of claim 10, wherein the processor is further configured to derive one or more measurements and metrics from the generated images, the one or more measurements and metrics related to displacement and movement of the tissue.

15. The system of claim 14, wherein the one or more measurements and metrics relate to brain motion to estimate intracranial pressure.

16. The system of claim 10, wherein the DENSE sequence of acquisition comprises a readout module comprising an imaging sequence adapted to acquire the images, wherein the imaging sequence comprises one of echo planar imaging (EPI), spiral imaging, turbo spin echo imaging, balanced steady state free precession (b-SSFP) imaging, and gradient echo (GRE) imaging.

17. The system of claim 10, further comprising an image data processor configured to process the images of the tissue, wherein the processing comprises one or more of phase unwrapping, displacement extraction, tissue tracking, temporal fitting, and mechanics indices calculation.

18. The system of claim 10, wherein the images of the tissue are utilized for quantitative assessment of biomarker parameters of tissue and organ, comprising one or more of mechanical properties parameters and time-resolved dynamic parameters.

\* \* \* \* \*